(12) United States Patent
Meric et al.

(10) Patent No.: US 12,036,427 B2
(45) Date of Patent: Jul. 16, 2024

(54) SYSTEM FOR CHARGED PARTICLE THERAPY VERIFICATION

(71) Applicant: Vestlandets Innovasjonsselskap AS, Bergen (NO)

(72) Inventors: Ilker Meric, Bergen (NO); Kristian Smeland Ytre-Hauge, Bergen (NO)

(73) Assignee: VESTLANDETS INNOVASJONSSELSKAP AS, Bergen (NO)

( * ) Notice: Subject to any disclaimer, the term of this patent is extended or adjusted under 35 U.S.C. 154(b) by 88 days.

(21) Appl. No.: 17/602,703

(22) PCT Filed: Apr. 8, 2020

(86) PCT No.: PCT/NO2020/050099
§ 371 (c)(1),
(2) Date: Oct. 8, 2021

(87) PCT Pub. No.: WO2020/209730
PCT Pub. Date: Oct. 15, 2020

(65) Prior Publication Data
US 2022/0161061 A1 May 26, 2022

(30) Foreign Application Priority Data
Apr. 10, 2019 (NO) .................................. 20190493

(51) Int. Cl.
*A61N 5/10* (2006.01)
*G01T 1/203* (2006.01)
*G01T 3/06* (2006.01)

(52) U.S. Cl.
CPC ............ *A61N 5/1071* (2013.01); *G01T 1/203* (2013.01); *G01T 3/06* (2013.01); *A61N 2005/1087* (2013.01); *A61N 2005/1092* (2013.01)

(58) Field of Classification Search
None
See application file for complete search history.

(56) References Cited

U.S. PATENT DOCUMENTS 5,880,469 A * 3/1999 Miller ...................... G01T 3/06
250/370.06
2007/0057194 A1* 3/2007 Ryan ......................... G01T 1/20
250/367

(Continued)

FOREIGN PATENT DOCUMENTS

EP 2977083 A1 1/2016
WO 2010/000857 A1 1/2010

(Continued)

OTHER PUBLICATIONS

EP 20787412.4; European Search Report; Dec. 8, 2022; 12 pages.

(Continued)

*Primary Examiner* — Edwin C Gunberg
(74) *Attorney, Agent, or Firm* — Kilpatrick Townsend & Stockton LLP (57) ABSTRACT

A system for charged particle therapy verification, comprising a first detector configured for detection of secondary particles emitted from a target irradiated with a charged particle beam, wherein the detector is configured to cause at least two consecutive elastic scatters in the detector for secondary particles of fast neutrons and two consecutive incoherent scatters followed by a third scatter, being one of: photoelectric effect, incoherent scatter or pair production for secondary particles of prompt gamma-ray types.

13 Claims, 7 Drawing Sheets

(56) References Cited

U.S. PATENT DOCUMENTS

| | | |
|---|---|---|
| 2010/0059687 A1 | 3/2010 | Balakin |
| 2014/0145088 A1* | 5/2014 | Prieels ................. A61N 5/1048 250/393 |
| 2015/0246244 A1 | 9/2015 | Sossong |
| 2017/0281977 A1 | 10/2017 | Beekman |
| 2018/0329089 A1* | 11/2018 | Bloser .................. G01T 1/2008 |
| 2019/0022415 A1 | 1/2019 | Boisseau |
| 2019/0094390 A1 | 3/2019 | Beddar |

FOREIGN PATENT DOCUMENTS

| | | |
|---|---|---|
| WO | 2011/143367 A2 | 11/2011 |
| WO | 2015/040225 A1 | 3/2015 |

OTHER PUBLICATIONS

Testa E et al: "Monitoring the Bragg peak location of 73 MeV/u carbon ions by means of prompt gamma-ray measurements", arxiv.org, Cornell University Library, 201 Olin Library Cornell University Ithaca, NY 14853, Sep. 1, 2008; XP080433481, DOI: 10.1063/1.2975841.

PCT/NO2020/050099, "International Search Report and Written Opinion," Mailed Jun. 29, 2020; 14 pages.

NO 20190493, "Norwegian Search Report," Mailed Dec. 14, 2019; 2 pages.

Ytre-Hauge, K. S. et al., A Monte Carlo feasibility study for neutron based real-time range verification in proton therapy. Scientific reports, Feb. 2019, vol. 9, Nr. 1, side 2011 [Hentet fra internett] (https://www.ncbi.nlm.nih.gov/pubmed/30765808?dopt=Abstract).

Weinfurther, K. et al., Model-based Design Evaluation of a Compact, High-Efficiency Neutron Scatter Camera. Nuclear Instruments and Methods in Physics Research, Section A: Accelerators, Spectrometers, Detectors and Associated Equipment, Mar. 2018, vol. 883, side 115-135 [Hentet fra internett] (https://www.sciencedirect.com/science/article/pii/S0168900217312238?via%3Dihub).

Marafini, M. et al., MONDO: a neutron tracker for particle therapy secondary emission characterisation. Physics in Medicine and Biology, Apr. 2017, vol. 62, Nr. 8, side 3299-3312.

Notice of Reasons for Rejection; JP Appl No. 2021-560559; Jan. 5, 2024_6 pages.

\* cited by examiner

SYSTEM FOR CHARGED PARTICLE THERAPY VERIFICATION

TECHNICAL FIELD

The present invention relates to the field of Charged Particle Therapy (CPT), ie. cancer therapy applying accelerated ion beams. More particular the invention relates to a detection system for real-time measurements of the range of charged particle beams in a target object or a human- or animal body as well as measurements of dose distribution. The system comprises plastic scintillator-based detector modules arranged in a matrix-like shape.

BACKGROUND

More than half of cancer patients receive radiotherapy as a part of their treatment (Delaney, G. et al., The role of radiotherapy in cancer treatment, Cancer, 2005, vol. 104, p. 1129-1137). The aim of curative radiotherapy (RT) is to inactivate all cancer cells by delivery of ionizing radiation to the tumour while at the same time minimize irradiation damage to surrounding healthy tissue. Interactions of charged particles such as protons, helium- and carbon-ions of an object or a tumor make them a very attractive alternative to conventional RT using Mega Voltage (MV) photons. This is because the dose from charged particles is deposited more precisely with a certain range or penetrating depth in a target object, and do not penetrate beyond that range. Furthermore, they deposit maximum amount of energy within in a narrow region called the Bragg-peak, offering higher tumour doses with significantly less dose to the surrounding healthy tissue. Charged particles also have an increased ability to kill the cancer cells compared to photons, i.e. the same physical dose produces a larger biological effect. Charged particle therapy (CPT) is therefore the preferred radiotherapy modality in treatment of some tumours at the skull base (chordomas, chondrosarcomas), in the management of childhood cancers (Patel, S. et al. Recommendations for the referral of patients for proton-beam therapy, an Alberta Health Services report: a model for Canada? Curr. Oncol., 2014, vol. 21, p. 251) and tumours of the central nervous system (Mishra, M. V. et al. Establishing Evidence-Based Indications for Proton Therapy: An Overview of Current Clinical Trials. Int. J. Radiat. Oncol., 2017, vol. 97, p. 228-235).

An important challenge associated with CPT is the considerable uncertainties in the particle range in tissue caused by tissue heterogeneities, anatomical changes over the course of the treatment, as well as inter- and intra-fractional organ motion. These uncertainties result in increased distal treatment margins in clinical protocols, and also limits the available beam irradiation angles as one due to the range uncertainties tries to avoid treatment fields pointing in the direction of healthy organs distal to the tumour. Thus, it has not been possible to exploit the full potential of the finite range of particles in tissue, especially when tumours are located near organs at risk and when organ motion may have adverse effects on the delivered dose. Therefore, the range of particle beams must be monitored during treatment with high precision of approx. 1-2 mm with the ultimate goal of minimizing the dose to healthy tissue.

As of today, the clinical solution developed for photon therapy and adapted to CPT to mitigate the effects of these uncertainties is adding safety margins around the tumour to define a so-called planning target volume and monitoring anatomical changes by image-guidance to reduce these margins as much as possible (van Herk, M., Errors and margins in radiotherapy. Semin. Radiat. Oncol. 2004, Vol. 14, p. 52-64). In CPT, the typical safety margins are about 3.5% of the nominal range+1 mm or a fixed 5 mm or even larger in regions with internal organ motion (Xie, Y. et al. Prompt Gamma Imaging for In Vivo Range Verification of Pencil Beam Scanning Proton Therapy. Int. J. Radiat. Oncol. 2017, vol. 99, p. 210-218).

WO2010/000857 A1 disclose a device and method for particle therapy range verification. The device is operated to detect prompt gamma rays produced when irradiating an object or a body, said device comprising a pin-hole camera and shielding means to avoid detection of stray particles.

EP2977083 B1 discloses an apparatus for particle therapy verification by detecting and quantifying prompt gamma-rays, using a collimator in front of a scintillator to obtain a one-dimensional dose related distribution of prompt gamma-ray profiles of the irradiated target.

Short Summary

A goal of the present invention is to overcome the problems of prior art, and disclose a system for real-time range and dose verification in CPT. Particularly, the invention provides an on-line detector capable of providing real-time measurements of the penetrating range of the charged particle beam in a target object or a body irradiated with the charged particles, such as protons, helium- or carbon-ions. Furthermore, it is an object of the invention to provide a verification of the delivered dose in a target or body irradiated by charge particles.

The invention solving the above mentioned problems is a system according to the independent claims.

An advantage of at least an embodiment of the invention, is that a full kinematic reconstruction of the angle and energy of the secondary prompt gamma-rays and fast neutrons s is possible.

The invention may in some embodiments improve the efficiency of a real-time range verification system with up to a magnitude, compared to prior art.

According to one aspect of the invention, it provides an improved system for real-time range verification and verification of the dose delivery in charged particle therapy.

According to another aspect of the invention, it provides verification of the penetrating depth of the charge particle beam with high degree of statistical precision.

In yet another aspect, the invention enables time-resolved two- and three-dimensional reconstruction of neutron and prompt gamma-ray production coordinates in a target or a patient with high degree of statistical precision at below disclosed particle beam intensities.

A further aspect of the invention is a range-verification and image guidance system in charge particle therapy with reduced physical size and increased flexibility compared to existing systems, which is important in a clinical context.

BRIEF DESCRIPTION OF THE DRAWINGS

The drawings illustrate embodiments or partial embodiments of the invention, and should not be regarded as limiting for the determination of the scope of protection.

FIG. 2. A illustrates in a schematic representation, an MCNP6.2 Monte Carlo simulation geometry setup for determining the secondary neutron and prompt gamma-ray detection efficiencies of the detector design: (1) proton beam, (2) water phantom, (3) detector, and (4) an angle of about 30° C.

FIG. 2 B illustrates in a graphical representation, a detected one dimentional, 1D, profile of secondary neutron and prompt gamma-ray production position distributions along the beam direction for a 200 MeV proton beam shown along with the "range landmark" positions for the corresponding neutron and prompt gamma-ray profiles: (1) range landmark position estimated from the detected neutron profile, (2) range landmark position estimated from the detected prompt gamma-ray profile, (3) detected neutron profile and (4) detected prompt gamma-ray profile.

FIG. 2 C illustrates in a graphical representation, an estimated linear fit of neutron (solid line) and prompt gamma-ray (dashed line) "range landmark" positions vs. nominal proton range in water wherein (1) is the range landmark positions at proton energy of 100 MeV, (2) range landmark positions at proton energy of 160 MeV, (3) range landmark positions at proton energy of 200 MeV and (4) range landmark positions of secondary neutrons and prompt gamma-rays at proton energy of 230 MeV.

FIG. 3 A illustrates neutron detection. Back-projection of an event cone based on detection of two consecutive (n,p) events in the sensitive volume of the detector: (2) $E_n$ Energy of incident neutron, (3) $1^{st}$ (n,p) collision, measurement of the recoil proton energy in the first collision, (5) the scattered neutron from the first event, (4) $2^{nd}$ (n,p) collision, used only for Time-of-Flight measurement, tau, and collision position. The sketch is given for "bar" shaped scintillators with (1) pixelated photodetectors for light read-out.

FIG. 3 B illustrates prompt gamma-ray detection. (6) Eγ—Energy of incident prompt gamma-ray, (7) $\Delta E_1$—measurement of energy deposited by the incident prompt gamma photon in the first incoherent scatter event, (8) $\Delta E_2$—measurement of energy deposited by the scattered photon in the second incoherent scatter event, (9) measurement of the collision position in the third scatter event that could be of any kind like incoherent, photoelectric or pair production. The sketch is given for "bar" shaped scintillators with (1) pixelated photodetectors.

FIG. 3 C illustrates very high energy neutron detection: Full kinematic reconstruction of the incidence angle and energy of the incoming high energy neutron based on tracking recoil protons from (n,p) events in the sensitive volume of the detector and the resulting back-projection of an event line instead of an event cone. This situation will be encountered in the context of CPT due to the extremely high energies of secondary neutrons (up to the primary beam energy in proton therapy and up to 300-400 MeV in carbon-ion therapy). (10) $E_n$ Energy of incident neutron, (11) $1^{st}$ (n,p) collision, measurement of the recoil proton energy in each penetrated scintillator bar as well as its direction in the first collision, (12) $2^{nd}$ (n,p) collision, measurement of the recoil proton energy in each penetrated scintillator pillar as well as its direction in the second collision. The sketch is given for "bar" shaped scintillators with (1) pixelated photodetectors for light read-out.

FIG. 4 A illustrates neutron arrival times as a function of initial neutron kinetic energy at 160 MeV initial proton beam energy.

FIG. 4 B illustrates prompt gamma-ray arrival times as a function of initial prompt gamma-ray energy at 160 MeV initial proton beam energy.

FIG. 4 C illustrates neutron (1) dominated area in arrival time (time of first interaction) vs. depth at 160 MeV initial proton beam energy and prompt gamma-ray (2) dominated area in arrival time (time of first interaction) vs. depth at 160 MeV initial proton beam energy.

FIG. 6 illustrates graphically Pulse Shape Discrimination (PSD).

FIG. 6 A illustrates a Figure-of-Merit method defining separation of neutron and prompt gamma-ray events. (1) mean of PSD signal distribution for prompt gamma-rays, $\mu_\gamma$, (2) mean of PSD signal distribution for neutrons, $\mu_n$, (3) Full Width at Half Maximum (FWHM) of the PSD signal distribution for prompt gamma-rays, FWHMγ, (4) Full Width at Half Maximum (FWHM) of the PSD signal distribution for neutrons, FWHMn.

FIG. 6 B illustrates charge-integration of neutron and prompt gamma-ray induced waveforms to discriminate between neutrons and prompt gamma-rays induced events. (1) Typical pulse shape (waveform) from a prompt gamma-ray induced event, (2) Typical pulse shape (waveform) from a neutron induced event, (3) Short integration of the pulse, $Q_{short}$, (4) Long integration of the pulse, $Q_{long}$. The PSD number is obtained as the ratio $(Q_{long}-Q_{short})/Q_{long}$.

FIG. 7 A illustrates uncertainties in neutron range landmarks obtained from detected neutron profiles. (1) Standard deviation of estimated neutron range landmarks as a function of primary proton intensity at 230 MeV, (2) Standard deviation of estimated neutron range landmarks as a function of primary proton intensity at 200 MeV, (3) Standard deviation of estimated neutron range landmarks as a function of primary proton intensity at 160 MeV, (4) Standard deviation of estimated neutron range landmarks as a function of primary proton intensity at 100 MeV FIG. 7 B illustrates uncertainties in prompt gamma-ray range landmarks obtained from detected prompt gamma-ray profiles.
(1) Standard deviation of estimated prompt gamma-ray range landmarks as a function of primary proton intensity at 230 MeV, (2) Standard deviation of estimated prompt gamma-ray range landmarks as a function of primary proton intensity at 200 MeV, (3) Standard deviation of estimated prompt gamma-ray range landmarks as a function of primary proton intensity at 160 MeV, (4) Standard deviation of estimated prompt gamma-ray range landmarks as a function of primary proton intensity at 100 MeV

EMBODIMENTS OF THE INVENTION

In the following description, various examples and embodiments of the invention are set forth in order to provide the skilled person with a more thorough understanding of
the invention. The specific details described in the context of the various embodiments and with reference to the attached drawings are not intended to be construed as limitations. Rather, the scope of the invention is defined in the appended claims.

The embodiments described below are numbered. In addition, dependent embodiments defined in relation to the numbered embodiments are described. Unless otherwise specified, any embodiment that can be combined with one or more numbered embodiments may also be combined directly with any of the dependent embodiments of the numbered embodiment(s) referred to.

In a first embodiment, the invention is a system for charged particle therapy verification, comprising;

a first detector configured for detection of secondary particles emitted from a target irradiated with a charged particle beam, wherein for detection of secondary neutrons, the detector is configured to produce at least two consecutive elastic scatters on hydrogen-1 nuclei, i.e. (n,p) scatters, in the sensitive volume of the detector, for detection of secondary prompt gamma-rays, the detector is configured to produce at least two consecutive incoherent prompt gamma-ray scatters followed by a third scatter of any kind in the sensitive volume of the detector.

In a first related embodiment, the detector comprises a scintillator, comprising an array of optically segmented organic scintillator elements, wherein the scintillator is configured to cause at least two consecutive elastic (n,p) scatters for the detection of secondary neutrons and two consecutive incoherent scatters followed by a third scatter of any kind for the detection of secondary prompt gamma-rays, wherein all mentioned scatter events are detected in distinct scintillator elements.

In a second related embodiment, the scintillator elements are columnar, and arranged in an array in a cross-section perpendicular to the length of the scintillator elements.

The scintillator may have a cross section of less than 30×30 cm$^2$ and a length/depth of 20 cm or more.

The individual scintillator elements may have a cross section of less than 2×2 cm$^2$.

The individual scintillator elements may have a cross section between 2×2 cm$^2$ and 0.5×0.5 cm$^2$.

The scintillator may comprise a reflective liner between at least some of the scintillator elements.

The reflective liner may be titanium dioxide or a reflector film such as for example an Enhanced Specular Reflector (ESR) film.

The scintillator elements may be spaced apart.

The scintillator elements may be organic.

The organic elements may be fast plastic scintillators with PSD capability or stilbene.

The scintillators may comprise both organic and inorganic scintillator elements.

The inorganic elements may be CeBr$_3$ or Lutetium-yttrium oxyorthosilicate (LYSO) crystals.

The scintillator may comprise a metallic casing around at least part of the scintillator elements. The metallic casing providing mechanical support to the assembly and potentially for providing shielding against scattered and secondary charged particles.

In a second embodiment that may be combined with any of the related embodiments of the first embodiment, the system comprises a photodetector array for scintillation light read-out, arranged at both ends of the scintillator elements.

The photodetector arrays may for example comprise of SiPMs (Silicon Photomultipliers) or MCP-PMs (Micro Channel Plate-Photomultipliers).

The photodetector may be arranged at each end of the scintillator elements.

In a third embodiment that may be combined with any of the related embodiments of the second embodiment, the system comprises a processing unit in connection with the photodetector array, wherein the processing unit is configured to estimate the direction and energy of the incoming fast neutrons and gamma-rays.

The processing unit may be configured to estimate the location of the nuclear interaction of the charged particle beam with the target.

The processing unit may be configured to estimate a distribution of a dose at the target.

The processing module may be configured for discrimination of the fast neutrons and prompt gamma-rays.

The processing module may be configured to discriminate the secondary neutrons from the prompt gamma-rays by pulse shape discrimination (PSD) or time-of-flight (ToF) measurements.

The processing module may be configured to discriminate the secondary neutrons from the prompt gamma-rays by simultaneously applying pulse shape discrimination (PSD) and time-of-flight (ToF) measurements.

The system, e.g. the processing module, may be configured to provide a real-time image of neutron and prompt gamma-ray production distributions in the target in two- or three-dimensions.

In a fourth embodiment that may be combined with any of the embodiments above, the system comprises a second detector, spatially separated from the first detector and configured for detection of secondary particles emitted from the target;

The second detector may comprise any combination of the same features as the first detector.

The processing unit may be in connection with the photodetector array of the second detector.

The first and second detectors may in an embodiment have a separate pre-processors for pre-processing the inputs from the respective photo-detectors before the pre-processed signal is forwarded to the processing unit.

In some embodiments the system may comprise of an array of optically segmented organic scintillators and an array of segmented inorganic scintillators.

Figure 6A:
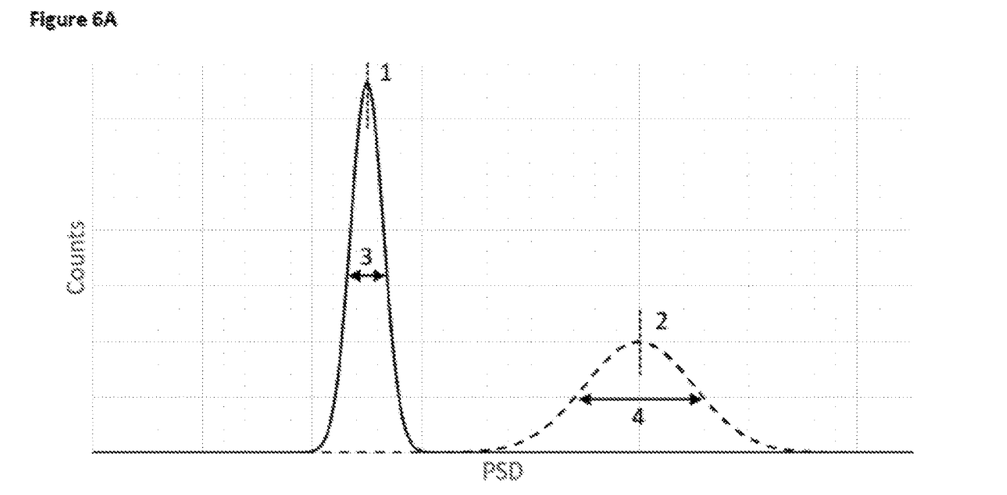
Figure 6B:
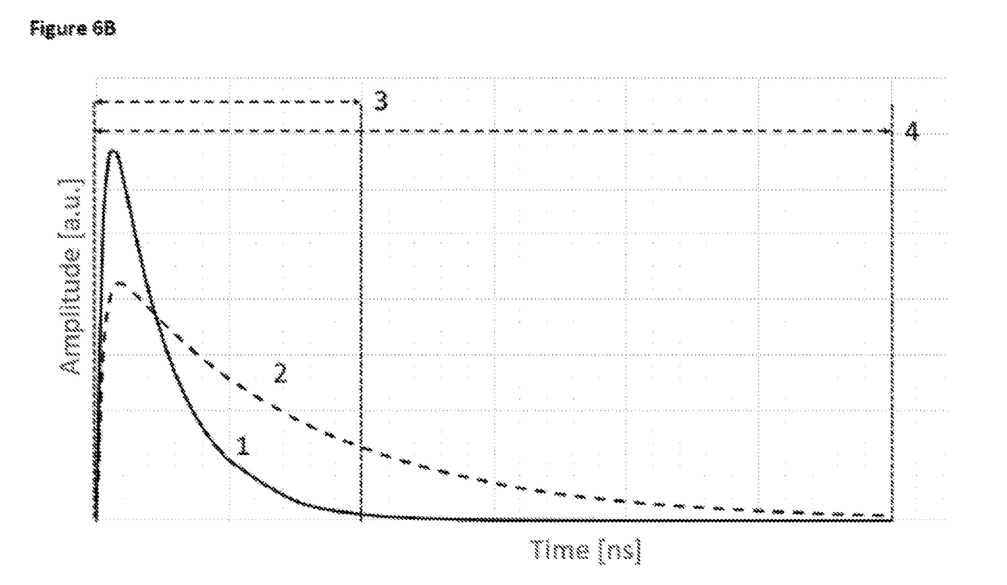

In one further embodiment, the detector comprises optically segmented "bars" or columns of organic scintillators and pixelated photodetectors mounted on each end of the detector enabling acquisition of two waveforms simultaneously for each event in each bar, FIG. 6A-B.

In the following, more details about a specific embodiment of a system according to the invention will be described.

The system comprises scintillator-based detector modules. A proton beam enters the target object or a human- or animal body and produces secondary particles along its path, until the proton beam stops inside the object or body. Among the secondary particles are secondary neutrons and prompt gamma-rays. A significant fraction of the secondary neutrons will leave the object or body, and some of these will reach the detector system. The same holds for the secondary prompt gamma-rays. The principle of the detection and imaging technique using the detector is described below. Traditionally, imaging of fast neutrons relies on the detection of two consecutive neutron elastic scatters on hydrogen-1 nuclei, i.e. (n,p) in an organic scintillator (Knoll, G. F. Radiation Detection and Measurement, John Wiley & Sons, 2010). In the first (n,p) scattering event, the energy of the recoil proton, Ep, is measured from the detected intensity of the scintillation light. The second (n,p) scattering event is used for both time-of-flight (TOF), given as τ (tau) in FIG. 3A, measurement and distance, given as d in FIG. 3A, between the first and second (n,p) scatter events.

Figure 3:
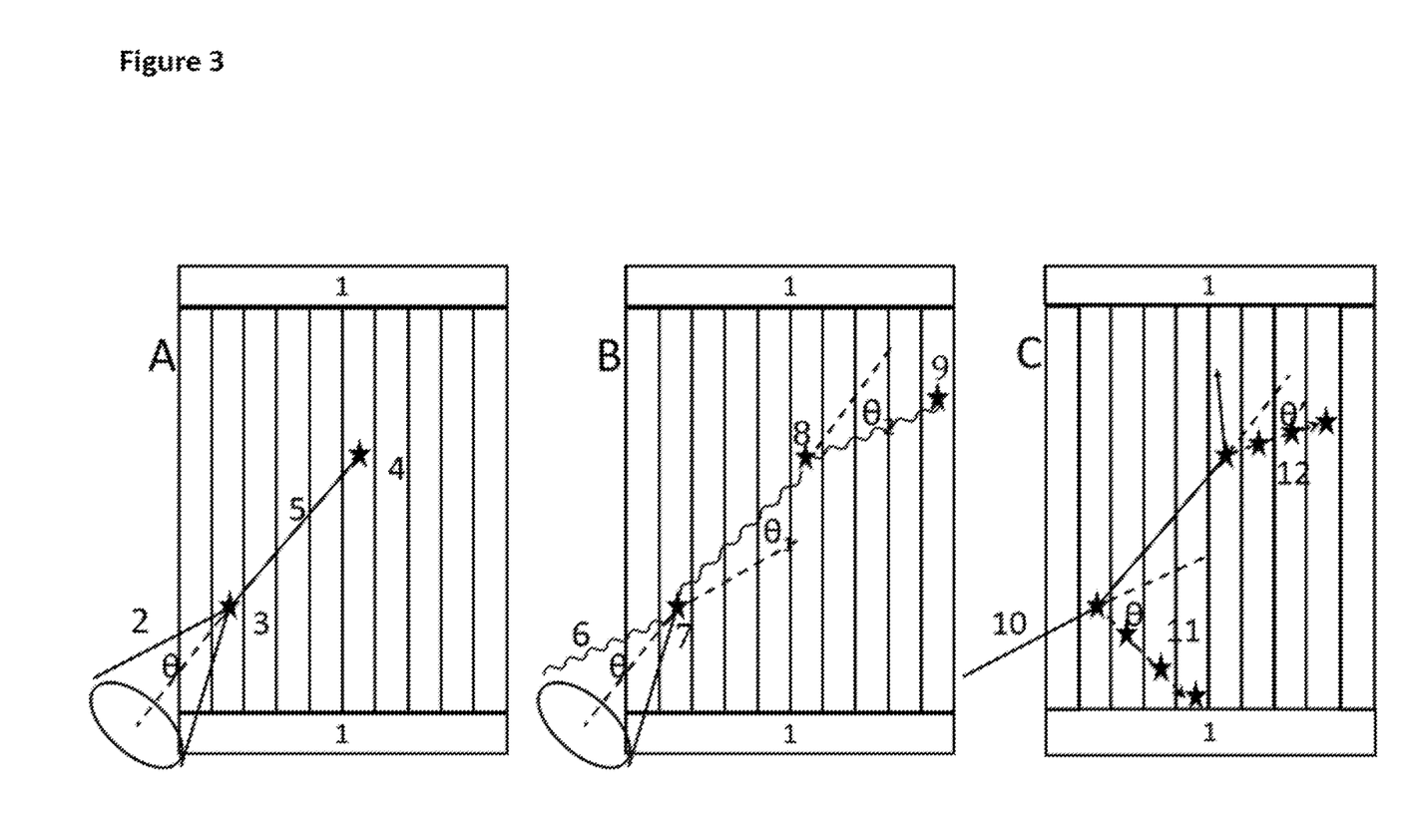
FIG. 3 illustrates principles of neutron and prompt gamma-ray detection and imaging in the detector.
Figure 4:
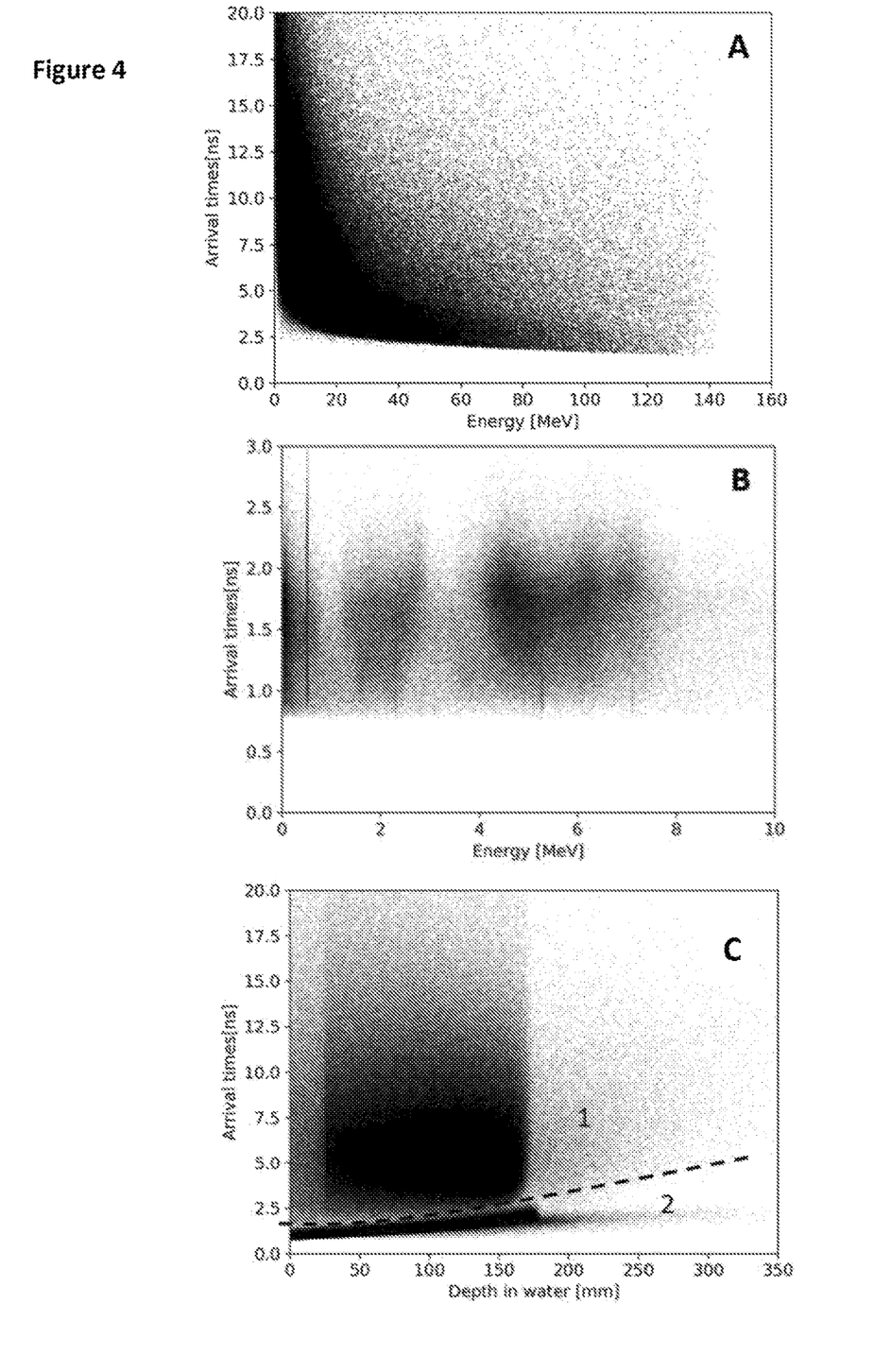
FIG. 4 illustrates graphically a distribution of prompt gamma-ray and neutron arrival times at the detector (the time of first interaction in the detector).

Based on the measured TOF and distance, the scattered neutron energy, En', is determined, $$E'_n = \frac{1}{2}m_n\left(\frac{d}{\tau}\right)^2$$

The energy of the incident neutron is then estimated as En=Ep+En' whereas the scattering angle of the incident neutron is given as θ=tan$^{-1}$√Ep/En'. However, due to the ambiguities in the determination of the azimuthal angle, an exact neutron incidence direction cannot be reconstructed. Instead, the neutron incidence is known to lie somewhere on the surface of an "event cone" as also depicted in FIG. 3A.

If a statistically sufficient number of such «event cones» are back-projected onto an image plane in the 3-dimensional space, the resulting image, obtained from intersection of the bases of these cones, reveals the location of the neutron emission.

In CPT, the situation as depicted in FIG. 3C is also a likely detection mechanism allowing more precise determination of the neutron emission positions. Extremely high energy neutrons (up to the primary particle beam energy) will, upon elastically colliding on hydrogen-1 nuclei, produce high energy recoil protons with sufficient energy to penetrate several scintillator elements.

Having a cross-sectional area of 0.25 cm² for each bar or column, recoil protons having kinetic energies in excess of 40 MeV can penetrate at least three elements. Tracking these protons and reconstructing their energies enable a full kinematic reconstruction of the angle and energy of the incident neutron. This allows back-projection of event lines instead of cones, which in turn reduce the uncertainty in the secondary neutron's point of origin as well as the uncertainty in the incident neutron's energy.

The computation of the event line comprises identification of the recoil proton track that originates from the first (n,p) collision. In non-relativistic kinematics of (n,p) elastic scatter collisions, the scattered neutron and proton recoil momenta are mutually orthogonal to each other. The recoil proton momenta from two (n,p) collisions is reconstructed, and a straight line joining the two collision sites is drawn giving the momentum of the scattered neutron from the first (n,p) collision. One of the two recoil proton momenta that is nearly perpendicular to this is then used to identify the direction of the scattered neutron and thus, the first (n,p) collision.

Reconstructing the energies and directions of both recoil protons from the two (n,p) interactions allows reconstruction of the incident neutron's energy and incidence angle with reduced uncertainties compared to the situation described above for the traditional detection of fast neutrons. As such, reconstruction eliminates ambiguities in the determination of the azimuthal angle, and eliminating ambiguities in the incoming neutron incidence angles allows reconstructing the neutron incidence direction which is now located along an "event line" instead of the surface of a cone.

In the described detector, similar principles apply to the reconstruction of the point of origin and energy of an incident prompt gamma-ray (FIG. 3B). A prompt gamma-ray photon reaches the detector and undergoes an incoherent, i.e. Compton scatter, interaction in the sensitive volume of the detector (1$^{st}$ scatter). The energy of the Compton recoil electron has to be measured as well as the scatter interaction position. In all cases, the interaction position is determined from the position of the responding scintillator element in the (x,y) directions. In the z-direction, the position is reconstructed from the waveforms collected through photodetectors at both ends of a given scintillator element.

The scattered prompt gamma-ray photon interacts once more in the sensitive volume of the detector through another incoherent scattering event (2$^{nd}$ scatter).

Again, the energy of the second Compton recoil electron has to be measured as well as interaction position of the second scattering event. The doubly scattered prompt gamma-ray interacts for a third time in the sensitive volume of the detector either through incoherent scatter, photoelectric effect or pair production (3$^{rd}$ scatter). Only the interaction position is needed. The information from the 3$^{rd}$ scatter and the 2$^{nd}$ scatter is used to determine the scattering angle in the 2$^{nd}$ incoherent scatter event.

The recoil energies of the electrons from the 1$^{st}$ and 2$^{nd}$ scatters are then used in conjunction with the scattering angle of the 2$^{nd}$ scatter event to determine the energy and incidence angle of the incoming prompt gamma-ray.

In an alternative situation a 3$^{rd}$ scatter is not required. In this case, correction factors need to be derived and applied to the measured recoil electron energy from the 2$^{nd}$ scatter to determine the energy of the scattered gamma-ray following the 1$^{st}$ scatter.

The information from these two alternative situations then allow for determining approximate incidence angles and energies of incident prompt gamma-rays. In this case, an "event cone" is reconstructed and the prompt gamma-ray emission point is said to lie somewhere on the surface of the cone.

As described above, in the depicted detector, gamma-ray incoherent scatters occur, and useful double or triple scatter efficiencies is obtained owing to the compactness of the detector which, allows simultaneous imaging of neutrons and prompt gamma-rays. The double and triple prompt gamma-ray scatter efficiencies may be further improved by increasing the overall size of the detector, i.e. by adding more detector elements.

A photodetector array is arranged on either end of the scintillator elements. The detection steps for neutrons and prompt gamma-rays as described above, produce optical photons in the scintillators, the intensities of which are proportional to the deposited energy in each scintillator. The optical photons undergo total internal reflection (TIR) at the scintillator air interfaces or be reflected back into the scintillator through the use of reflectors with high reflectivity. In this manner, the optical photons propagate to either end of the scintillator bars where the photodetectors are mounted in an array. In the photodetectors, the arriving optical photons are then converted to electrical charge.

A processing unit is arranged in communication with the photodetector array configured for read-out of waveforms and discrimination between photon- and neutron induced waveforms. The unit receives waveforms to be processed from the photodetector arrays. The pulse is then sensed by the read-out circuitry. In order to perform simultaneous imaging of neutrons and gamma-rays, the pulses induced by both must be discriminated.

Discrimination between photon- and neutron-induced signals can be performed using either pulse shape discrimination (PSD) or Time of Flight (TOF) measurements. The two will be explained below.

Pulse shape discrimination (Söderström, P. A., et al., Digital pulse-shape discrimination of fast neutrons and rays. Nuclear Instruments and Methods in Physics Research Section A: Accelerators, Spectrometers, Detectors and Associated Equipment, 2008, vol. 594, p. 79-89) is illustrated in FIG. 6A-B. The signals induced by incident photons and neutrons will differ for certain organic scintillator types (such as liquids and plastics) with respect to their time-intensity profiles. In organic scintillators, fast neutron induced events result in longer lived scintillation pulses compared to gamma-ray induced events. In order to discriminate between neutron-induced events and those that are induced by incident prompt gamma-rays, integration of the recorded signal pulses is performed in two parts (long and short), FIG. 6B. In this approach PSD methods rely on a long, $Q_{long}$ and a short, $Q_{short}$, integration of these signals and deriving a third signal based on the ratio of the short and long integrated pulses, PSD=$(Q_{long}-Q_{short})/Q_{long}$.

One quantitative approach for PSD discrimination is to use Figure-of-Merit (FoM) to quantify the quality of the PSD of organic scintillators to be deployed in the detector as illustrated in FIG. 6A. The FoM is given as:

$$FOM = \frac{\mu_n - \mu_\gamma}{FWHM_\gamma + FWHM_n}$$

Where $\mu_\gamma$ is mean of PSD signal distribution for prompt gamma-rays, $\mu_n$ is mean of PSD signal distribution for neutrons, $FWHM_\gamma$ (Full Width at Half Maximum) of the PSD signal distribution for prompt gamma-rays and F FWHM (Full Width at Half Maximum) of the PSD signal distribution for neutrons.

Figure 5:
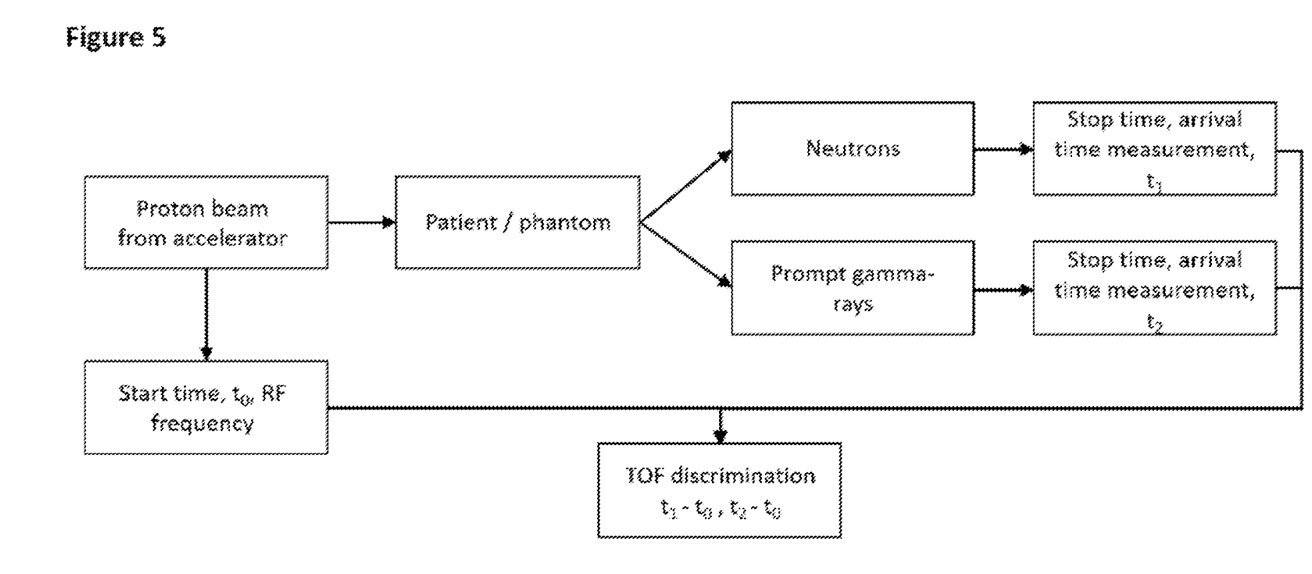
FIG. 5 illustrates in a block diagram of an embodiment of the system according to the invention, based on Time-of-Flight (ToF) measurements and discrimination.

Measurements of the arrival times of prompt gamma-rays and neutrons, i.e. time-of-flight (ToF) measurements (FIG. 5) can be an additional means of discriminating between neutron- and prompt gamma-ray-induced events in the sensitive volume of the detector. The arrival times of prompt gamma-rays versus neutrons show clear differences. The high energy neutrons will typically arrive at the detector with a few ns of delay compared to prompt gamma-rays. Depending on the initial distance between the point of origin and the detector surface and neutron moderation in the target itself, incident secondary neutrons will show a variation in arrival times, increasing for lower energies and greater distances.

Most prompt gamma-rays reach the detector within 2-3 ns, measured as the time it takes between the incidence of the proton pencil beam on a water phantom until the first incoherent scatter event registered in the sensitive volume of the detector. Neutrons show a large variation depending on energy and depth at which they were produced in the water phantom. Most neutrons reach the detector within 5-6 ns with a long tail up to about 30-40 ns.

The scintillator elements or "bars" provide containment of scintillation light from neutron and prompt gamma-ray scatter events along a single element through air gaps and lining with reflective material. This structure eliminates cross-talk between individual channels and thus reduces the data throughput, and complexity of subsequent data analysis significantly as compared to a monolithic approach.

The amplitudes and relative timing of the two waveforms from the photodetectors can then be used to reconstruct the collision position along the height of a given bar (the z-axis). The bar dimensions, the scintillation light yield, the scintillation decay time constant, light channeling efficiency through the bars, quantum efficiency of the photodetector and transit time spread of the photodetector are parameters that will ultimately affect the precision with which scintillation light production positions (i.e. collision positions along the length of a given scintillator bar), and recoil particle (protons and electrons) energies can be estimated.

The physical thickness of each bar ultimately determines the precision in the estimation of the collision position along the x- and y-axes whereas the statistical uncertainties in the estimation of the collision position along the z-axis will predominate the overall uncertainties in estimating the neutron and prompt gamma-ray collision positions.

In an embodiment, the means for discrimination of neutrons and prompt gamma-rays comprises scintillators with pulse shape discrimination (PSD) capabilities, such as Stilbene and PSD plastic scintillators.

These are scintillation crystals where neutron induced events typically produce longer scintillation light pulses than prompt gamma-ray induced events (Pozzi, S. A. et al., Pulse shape discrimination in the plastic scintillator EJ-299-33. Nucl. Instrum. Methods Phys. Res. Sect. Accel. Spectrometers Detect. Assoc. Equip., 2013, vol. 723, p. 19-23).

A Monte Carlo (MC) simulation study to reveal the expected detection efficiencies of the depicted detector as a dual imaging device able to detect both neutrons and prompt gamma-rays produced by protons impinging on a water phantom using MCNP6.2 has been performed. MCNP6.2 (Goorley, T. et al. Initial MCNP6 Release Overview. NT, 2012, vol. 180, p. 298-315) is a MC code system for the simulation of the interactions and passage of neutrons, photons, electrons, positrons, alphas, protons and other heavier ions (a total of 37 different particle types) in arbitrary geometries and materials.

The pertinent MC simulations include mono-energetic beams of protons with energies of 100, 160, 200 and 230 MeV and a water phantom whereas the depicted detector was modelled as a monolithic 10×10×20 $cm^3$ "block" of a hydrogen-rich liquid organic scintillator (density of 0.959 $g/cm^3$ and H/C ratio of 1.25). At each energy, the proton beam intensity was set to $1 \times 10^9$ protons and the detector was placed at a location just above the expected, nominal Bragg-peak location.

Figure 1:
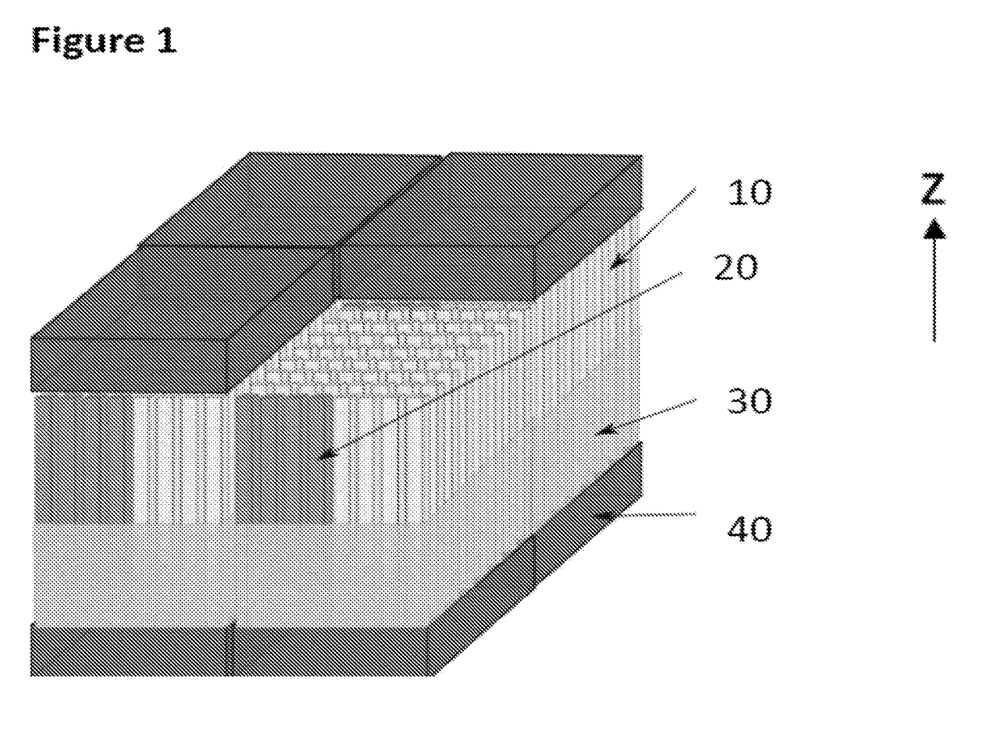
FIG. 1. Illustrates a conceptual design of the detector that is based on optically segmented bars of organic scintillators: (10) Scintillator bars, (20) reflective tape, (30) aluminium casing, (40) photo multipliers for light read-out.
Figure 2:
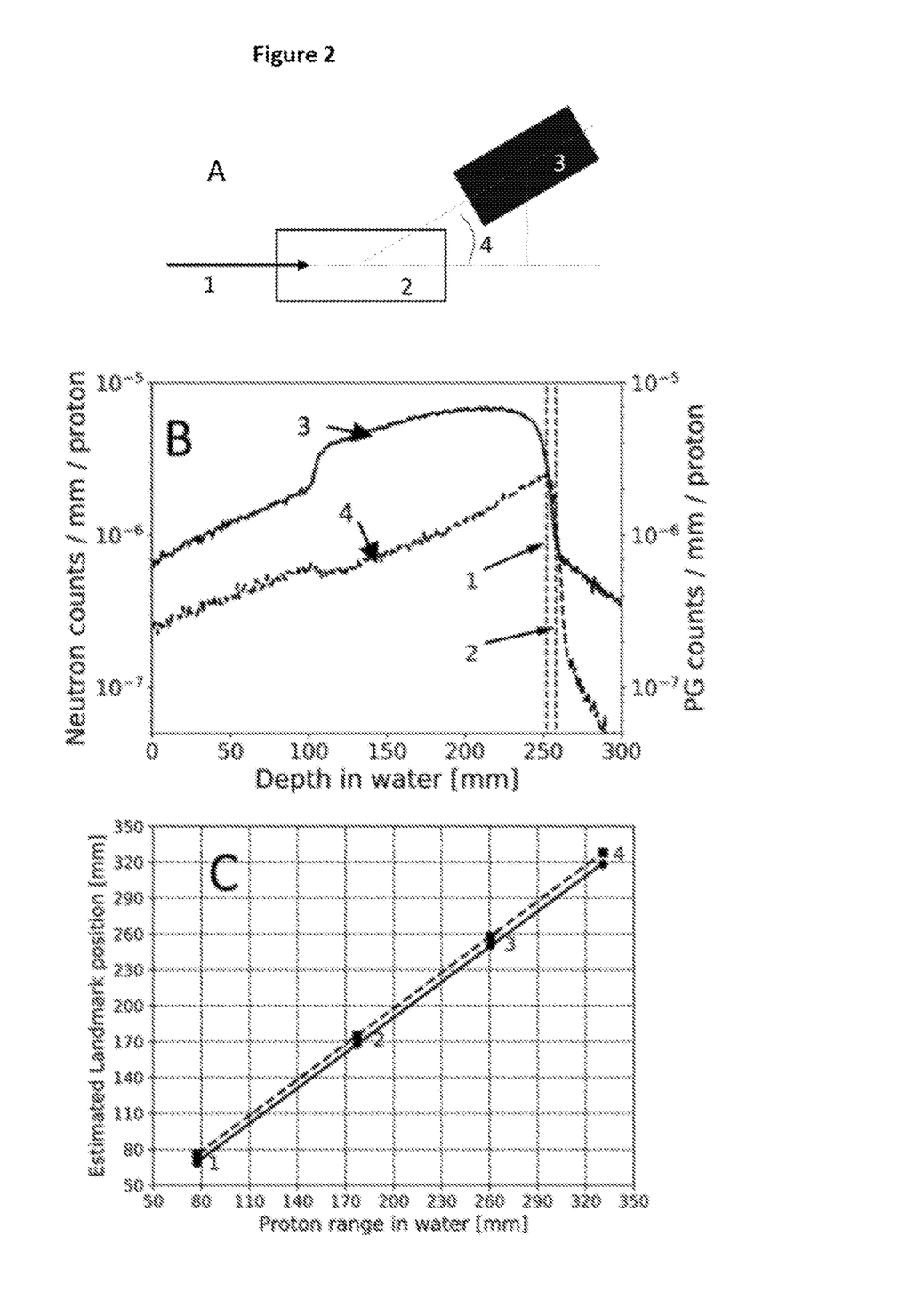

An example of the simulated geometry is shown in FIG. 2A. The number of secondary neutrons having their first two interactions as elastic scattering off hydrogen-1 nuclei in the detector volume was recorded. In addition, the number of prompt gamma-rays having their first two interactions as incoherent, i.e. Compton, scattering events were recorded. The double (n,p) scatter rates of incident neutrons per primary proton as well as double incoherent scatter rates of incident prompt gamma-rays per primary proton and their corresponding statistical uncertainties (one standard deviation) are given in the following table:

| Proton energy [MeV] | Double (n, p) scatter rate (fast neutrons) | Standard dev. | Double incoherent scatter rate (prompt gamma) | Standard dev. |
|---|---|---|---|---|
| 100 | $5.7 \times 10^{-4}$ | $7.6 \times 10^{-7}$ | $1.6 \times 10^{-4}$ | $3.9 \times 10^{-7}$ |
| 160 | $9.7 \times 10^{-4}$ | $9.8 \times 10^{-7}$ | $2.2 \times 10^{-4}$ | $4.6 \times 10^{-7}$ |
| 200 | $9.9 \times 10^{-4}$ | $9.9 \times 10^{-7}$ | $2.3 \times 10^{-4}$ | $4.8 \times 10^{-7}$ |
| 230 | $8.9 \times 10^{-4}$ | $9.5 \times 10^{-7}$ | $2.3 \times 10^{-4}$ | $4.8 \times 10^{-7}$ |

The results reveal that the double incoherent scatter rates for incident prompt gamma-rays will be lower by about a factor of 5 compared to the double (n,p) scatter rates for incident neutrons. The reduction in the efficiency is expected to be higher when applying more stringent constraints, i.e. requiring also a third interaction to take place in the sensitive volume of the detector.

Although the detector is composed of organic scintillators with low density and low atomic number, the compactness and the overall size of the detector compensate for this. Thus, useful efficiencies, also for highly energetic prompt gamma-rays, are achievable. The efficiencies of state-of-theart real-time range verification systems based on prompt gamma-ray imaging range from $10^{-5}$ to $5.6 \times 10^{-5}$ prompt gamma-ray counts/proton, or even lower for Compton cameras and collimated cameras. The detector design depicted here can therefore achieve unprecedented detection efficiencies, even for prompt gamma-rays alone The efficiencies will be unmatched due to the fact that the detector will be sensitive to both neutrons and prompt gamma-rays, and will combine data from these two particle species.

In addition, the profiles of detected neutrons are favorable, with a steep fall-off just proximal to the Bragg-peak as shown in FIG. 2B. To obtain the "range landmarks" that can be correlated with the primary proton beam range, a simple logistic function was fitted to the neutron profiles whereas a Savitsky-Golay filter was applied to the prompt gamma-ray profiles for further smoothing of the resulting detection profiles. For both neutron and prompt gamma-ray profiles, the inflection point positions were taken as a "range landmark", FIG. 2C.

The collected datasets for primary proton beam intensity of $1 \times 10^9$ were then divided into 10 equal chunks corresponding to a proton intensity of $1 \times 10^8$ protons. The calculations of range landmarks were then repeated for each of these chunks to enable a statistical analysis of the results.

Next, the original datasets were divided into 20 equal chunks corresponding to a proton intensity of $5 \times 10'$ protons. The range landmarks were re-calculated, again for ten trials. The procedure was repeated to obtain the statistical uncertainties in range landmark estimates at lower proton beam intensities.

Figure 7A:
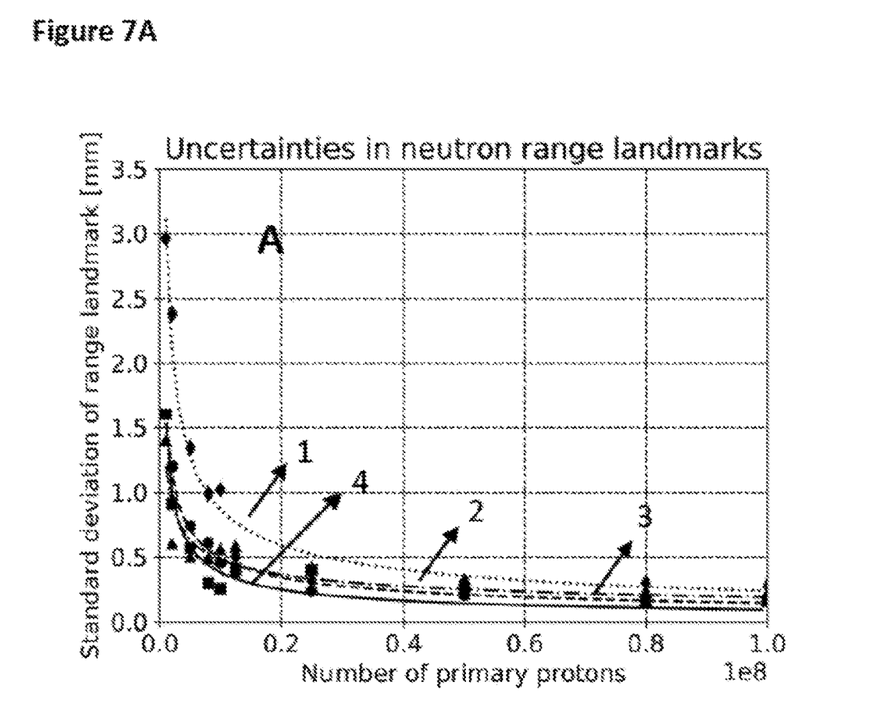
Figure 7B:
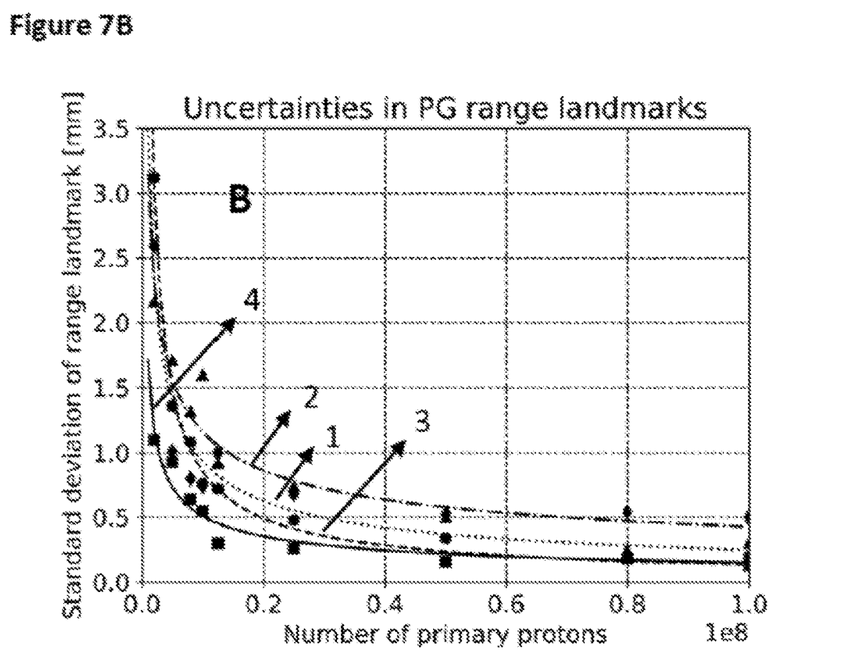

The statistical precision in the estimation of range landmarks obtained from both neutron and prompt gamma-ray profiles reveal that sub-millimetric precision may be possible to achieve down to initial proton beam intensities of about $1 \times 10^7$ protons, see FIGS. 7A and 7B; which is highly encouraging in relation to MC simulations of state-of-the-art range verification systems.

Simulations repeated at 100, 160, 200 and 230 MeV proton beam energies reveal also that the range landmark positions from both neutron and prompt gamma-ray profiles are linearly correlated with the Bragg-peak position as shown in FIG. 2C.

In conclusion, the depicted detector concept for real-time range verification in and image-guidance in CPT is clearly justified by the superior detection efficiencies, detected neutron and prompt gamma-ray profiles, possibility of performing 2D and 3D imaging in real-time as well as the possibility of unification of neutron and prompt gamma-ray imaging in a single, compact device.

The example is for illustration purpose only and illustrates that the depicted detector system can be used to detect neutrons and prompt gamma-rays with a superior detection efficiency with respect to the state-of-the-art range verification systems in CPT. The detection of both neutrons and prompt gamma-rays enables a more accurate determination and verification of the treatment through a more precise determination of the Bragg-peak position in the target.

In the exemplary embodiments, various features and details are shown in combination. The fact that several features are described with respect to a particular example should not be construed as implying that those features by necessity have to be included together in all embodiments of the invention. Conversely, features that are described with reference to different embodiments should not be construed as mutually exclusive. As those with skill in the art will readily understand, embodiments that incorporate any subset of features described herein and that are not expressly interdependent have been contemplated by the inventor and are part of the intended disclosure. However, explicit description of all such embodiments would not contribute to the understanding of the principles of the invention, and consequently some permutations of features have been omitted for the sake of simplicity or brevity.

The invention claimed is:

1. A system for charged particle therapy verification, comprising:
   a detector comprising an array of optically segmented scintillator elements, the detector configured for detection of secondary particles emitted from a target irradiated with a charged particle beam, wherein:
   the detector is configured to produce at least two consecutive elastic (n,p) scatters in a sensitive volume of the detector for secondary fast neutrons, and two consecutive incoherent scatters followed by a third scatter event of any kind for the detection of secondary prompt gamma-rays, wherein the at least two consecutive elastic (n,p) scatters, the two consecutive incoherent scatters, and the third scatter event of any kind are detected in distinct scintillator elements of the array of optically segmented scintillator elements.

2. The system of claim 1, wherein the third scatter event comprises one of: photoelectric effect, incoherent scatter, or pair production for secondary prompt gamma-rays.

3. The system of claim 1, wherein the scintillator elements are columnar and arranged in an array in a cross-section perpendicular to a length of the scintillator elements.

4. The system of claim 1, comprising a photodetector array arranged at either end of the array of optically segmented scintillator elements.

5. The system of claim 4, comprising a processing unit in connection with the photodetector array, wherein the processing unit is configured to estimate directions and energies of the incident fast neutrons and the incident prompt gamma-rays.

6. The system of claim 5, wherein the processing unit is configured to estimate a location of a nuclear interaction of the charged particle beam with the target.

7. The system of claim 5, wherein the processing unit is configured to estimate a distribution of a dose at the target from detected and reconstructed secondary fast neutron and prompt gamma-ray production position profiles.

8. The system of claim 5, wherein the processing unit is configured for discrimination of the incident fast neutrons and the incident prompt gamma-rays.

9. The system of claim 8, wherein the processing unit is configured to discriminate between the incident fast neutrons and incident prompt gamma-rays by pulse shape discrimination (PSD) or time-of-flight (ToF) measurements.

10. A method for charged particle therapy verification, comprising:
    detecting, by a system comprising a detector, secondary particles emitted from a target irradiated with a charged particle beam, wherein the detector is configured for producing at least two consecutive elastic (n,p) scatters in a sensitive volume of the detector for secondary fast neutrons, and two consecutive incoherent scatters followed by a third scatter event of any kind for the detection of prompt gamma-rays, wherein the at least two consecutive elastic (n,p) scatters, the two consecutive incoherent scatters, and the third scatter event of any kind are detected in distinct scintillator elements.

11. The method of claim 10, further comprising:
    reconstructing emission profiles of the secondary fast neutrons and prompt gamma-rays.

12. The method of claim 11, further comprising:
   estimating a charged particle range in the target based on the reconstructed emission profiles.

13. The method of claim 11, further comprising: estimating a distribution of a dose at the target.

* * * * *